United States Patent [19]
Alcock et al.

[11] Patent Number: 5,804,094
[45] Date of Patent: Sep. 8, 1998

[54] LOW BASE NUMBER SULPHONATES

[75] Inventors: Kenneth Alcock, Oxfordshire, United Kingdom; Dominique Moulin, N. D. de Gravenchon, France; John Arthur Cleverly; Charles Herbert Bovington, both of Oxfordshire, United Kingdom

[73] Assignee: Exxon Chemical Patents, Inc., Wilmington, Del.

[21] Appl. No.: 875,251

[22] PCT Filed: Feb. 27, 1996

[86] PCT No.: PCT/EP96/00812

§ 371 Date: Sep. 3, 1997

§ 102(e) Date: Sep. 3, 1997

[87] PCT Pub. No.: WO96/26919

PCT Pub. Date: Sep. 6, 1996

[30] Foreign Application Priority Data

Feb. 28, 1995 [GB] United Kingdom ............... 9504034

[51] Int. Cl.$^6$ ................ C07C 303/02; C10M 129/00
[52] U.S. Cl. ................ 252/18; 252/33; 252/33.4; 252/39; 252/40.7; 252/33.2; 562/115
[58] Field of Search ................ 252/18, 33, 39, 252/40.7; 562/115

[56] References Cited

U.S. PATENT DOCUMENTS

| | | | |
|---|---|---|---|
| 4,764,295 | 8/1988 | Le Coent | 252/33.2 |
| 5,281,345 | 1/1994 | Crawford et al. | 252/18 |
| 5,684,184 | 11/1997 | Alcock et al. | 562/97 |

FOREIGN PATENT DOCUMENTS

| | | |
|---|---|---|
| 0013807 | 8/1980 | European Pat. Off. . |
| 1575957 | 10/1980 | United Kingdom . |

*Primary Examiner*—Johann Richter
*Assistant Examiner*—Laura R.C. Lutz
*Attorney, Agent, or Firm*—Ohlandt, Greeley, Ruggiero & Perle

[57] ABSTRACT

Low base number (LBN) sulphonates derived from high molecular weight sulphonic acids have low viscosity, are chloride free and are not skin sensitisers. In their preparation, neutralisation of high molecular weight sulphonic acids or partially neutralised soaps of high molecular weight sulphonic acids is completed by the use of a high base number sulphonate in conjunction with a carboxylic acid. The process does not require the use of chloride containing promoters and produces low chloride products which do not skin on exposure to air.

21 Claims, No Drawings derivatives thereof; the process utilises chloride containing salts and carboxylic acids such as formic acid. The products have relatively low viscosity but contain chloride.

LOW BASE NUMBER SULPHONATES

This application is a 371 of PCT/EP96/00812 filed Feb. 27, 1996.

The present invention relates to low base number sulphonates and to processes for the production of these sulphonates. The invention also relates to oil based compositions containing these low base number sulphonates.

Basic or neutral sulphonates may be used as additives in lubricating oils for petrol engines and diesel engines for example for vehicles or marine engines. Neutral and low base number sulphonates function primarily as detergents to keep engine surfaces clean. High base number sulphonates are primarily used to neutralise acids produced in the oil during use. These sulphonates may help to inhibit corrosion.

Neutral and low base number sulphonates for use as oil additives are usually prepared by the neutralisation of a sulphonic acid with a basic salt such as a basic calcium salt e.g. calcium oxide or hydroxide in a suitable diluent oil. The sulphonate product may be a mixture of a number of species. In addition dispersed calcium hydroxide may be present.

The product of this process may display some basicity, for example if the basic salt is added in stoichiometric excess to that required for complete neutralisation of the sulphonic acid, or some other basic component is present. The product in this case is said to be overbased.

The neutral metal salts of typical sulphonic acids are extremely viscous materials and would have a TBN, as measured by ASTM D-2896, of zero. Methods have been sought which permit lower viscosity products to be prepared. This has been achieved by the incorporation of chloride, formate and hydroxide ions into the product. The products of these techniques are not truly neutral but are slightly overbased in that they contain more base than that required to react stoichiometrically with the sulphonic acid.

In particular, it is difficult to produce low base number sulphonates from synthetic high molecular weight sulphonic acids, ie synthetic acids of average molecular weights of 500 or greater, which also have low viscosity. If this is attempted, high viscosity soaps or high viscosity sulphonates are produced which have a lower than expected base number. One way of overcoming this, as indicated previously, is by adding more base which tends to reduce viscosity and increase the base number of the product. However this addition of for example excess $Ca(OH)_2$ produces free hydroxyl which is believed to be associated with a skinning effect on exposure to air on the surface of the sulphonate. Skinning is an undesirable property of low base number sulphonates. Viscosity can be controlled to some extent by the addition of halide as outlined above.

U.S. Pat. No. 4,764,295 discloses a process for the production of low base number sulphonates from sulphonic acids which have alkyl radicals of $C_{15}$ to $C_{40}$; the process utilises chloride containing salts and carboxylic acids such as formic acid. The products have relatively low viscosity but contain chloride.

High base number sulphonates are generally prepared by a process of neutralisation with excess base (overbasing) followed by carbonation. Typically the sulphonic acid is neutralised with excess basic metal oxide or hydroxide in a suitable diluent. Some of the excess basic metal oxide or hydroxide is converted to metal carbonate via carbonation. Typically the reaction is carried out in the presence of hydrocarbon and/or polar solvents such as toluene/methanol and diluent oil; some or all of these solvents may be subsequently removed. The resulting product is a colloidal dispersion, in a diluent oil, of sub-micron particles of $CaCO_3$ and $Ca(OH)_2$ which are sterically stabilised by the calcium sulphonate species produced by the reaction.

Sulphonates have been prepared from synthetic sulphonic acids which have in turn been prepared for example by the sulphonation of $C_{12}$ to $C_{60+}$ alkyl substituted benzene, or xylene or toluene compounds and mixtures thereof. It has been found that some synthetic sulphonic acids are difficult to neutralise with for example calcium hydroxide or lime to produce sulphonates which have acceptable properties; the attempted neutralisation results in the production of gelatinous products which for example are solid at room temperature. This is a particular problem when trying to prepare Neutral or Low Base Number Sulphonates from such sulphonic acids. Methods have been proposed to overcome this problem associated with synthetic sulphonic acids. One such method for sulphonic acids of molecular weight 480–540 is described in GB 1 575 957 wherein a large stoichiometric excess, over that required for neutralisation of the sulphonic acid, of calcium hydroxide is added to a portion of the sulphonic acid in a diluent to produce a reaction mixture; the remainder of the sulphonic acid is subsequently added to the mixture, this addition being less than that which would be required to fully react with the remaining calcium hydroxide in the mixture. In addition a solution containing a source of chloride ion is added to the mixture after the calcium hydroxide or lime addition; the chloride ion is believed to act as a fluidiser for the product formation and is beneficial in enabling the production of fluid, filterable products from certain sulphonic acids such as synthetic sulphonic acids. The addition of chloride promoter prevents the formation of gelatinous products; however, the final product, contains chloride.

The presence of chloride in calcium sulphonates and other metal sulphonates is a problem from a waste disposal and environmental point of view. When compositions containing such sulphonates are destroyed, e.g. by incineration, harmful chlorinated and polychlorinated biphenyls may be produced. Waste disposal of compositions based on chloride containing sulphonates is therefore a problem; it would be advantageous to be able to produce chloride-free low base number sulphonates especially those derived from high molecular weight sulphonic acids without a loss of the beneficial properties associated with the use of chloride in their manufacture.

In addition to the above mentioned problems, low base number sulphonates have also been found to sensitise the skin, which may lead to dermatological problems for those exposed to them during handling, or to requirements for specific handling. This tendency of a material to be a skin sensitiser is determined by skin patch testing.

Thus, a need exists for low base number sulphonates and methods for making such sulphonates which do not have the foregoing problems of high levels of chloride ions, high viscosity and sediment, high levels of free hydroxyl ion and skinning, and which do not display skin sensitisation problems.

Furthermore, a need exists for lubricating oil formulations which have low levels of phosphorus because it may contaminate automobile catalytic converters and poison the catalytic material. One of the most significant sources of phosphorus in lubricating oils are antiwear agents such as the zinc dialkyldithiophosphates. However, it is difficult to formulate with reduced levels of such antiwear agents and improve or maintain acceptable antiwear properties.

According to the present invention there is provided a calcium or Group 1 metal low base number sulphonate composition comprising from at least 10%, preferably at least 20%, by weight of at least one high molecular weight sulphonate, a metal carboxylate and diluent, wherein the sulphonate composition is low in hydroxyl, and low in halide ions. Such a composition does not form a skin on exposure to air.

In a further aspect the invention provides a method for the preparation of a calcium or Group 1 metal low base number sulphonate composition which comprises neutralising a high molecular weight sulphonic acid, or a partially neutralised soap thereof, and a carboxylic acid with a high base number sulphonate.

It is preferred that the low base number sulphonate compositions comprise 20 to 80 wt %, preferably at least 40% and most preferably 40 to 60% by weight of metal sulphonate.

It is also preferred that the kinematic viscosity of the low base number sulphonate compositions at 100° C. is less than 1000 centistokes (cS), preferably 700 cS or less e.g. 300 cS or less, most preferably 150 cS or less and most preferably in the range 30–100 cS (1 cS=$10^{-6}m^2s^{-1}$).

"Low in halide ions" means having a chloride content of 100 ppm by weight or less, preferably 50 ppm or less and most preferably 20 ppm or less.

"Low in hydroxyl" means having 0.5% by weight or less based on the total weight of the composition, preferably 0.25% by weight or less and most preferably 0.1 to 0.2% by weight or less of hydroxide expressed as the Ca or Group 1 metal hydroxide.

The terms "low base number" and "high base number" as used to define sulphonates should be understood in relation to ASTM D2896-88 "Standard Test Method for Base Number of Petroleum Products by Potentiometric Perchloric Acid Titration". This test method is concerned with the determination of basic constituents in petroleum products by potentiometric titration with perchloric acid in glacial acetic acid. The result of this test method is quoted as a base number which is the base equivalence in mg KOH $g^{-1}$. Thus the term "low base number" refers to numerical values of base number which are less than 50 mg KOH $g^{-1}$ and the term "high base number" refers to numerical values of base number which are greater than 50 mg KOH $g^{-1}$ and may be as high as 400 mg KOH $g^{-1}$ or even higher e.g. 600. A sulphonate is neutral if no basic or acidic constituents can be detected by titration.

"High molecular weight sulphonate" means a sulphonate which has been prepared from the neutralisation of a high molecular weight sulphonic acid as defined herein below.

"High molecular weight sulphonic acid" means having a number average molecular weight of 500 or greater, preferably 600 or greater, being an oil soluble synthetic sulphonic acid, which may be an alkyl sulphonic acid, or an alkaryl sulphonic acid. The high molecular weight sulphonic acid may be a single high molecular weight sulphonic acid or it may be a mixture of different sulphonic acids, that is a mixed sulphonic acid. The mixed sulphonic acid may be a mixture of high molecular weight sulphonic acids, ie sulphonic acids which have a number average molecular weight of 500 or greater preferably 600 or greater. The mixed sulphonic acid may be a mixture of high molecular weight sulphonic acid or acids, with lower molecular weight sulphonic acid or acids which have a number average molecular weight of less than 500. When the mixture is a mixture of high molecular weight sulphonic acid or acids and low molecular weight sulphonic acid or acids, the proportion by mass of high molecular weight sulphonic acid(s) in the mixture is at least 50%, preferably 60% and most preferably 75%, or is such that the number average molecular weight of the mixture is 500 or greater and most preferably is 600 or greater. Number average molecular weight may be determined by available techniques such as that described in ASTM D-3712.

It is preferred that the high molecular weight sulphonic acid is an alkaryl sulphonic acid such as for example an alkyl benzene sulphonic acid, alkyl toluene sulphonic acid or alkyl xylene sulphonic acid. It is also preferred that it is a mixed sulphonic acid of $C_{15}$ to $C_{60}$ and higher alkyl benzene or $C_{15}$ to $C_{60}$ and higher alkyl xylene or $C_{15}$ to $C_{60}$ and higher alkyl toluene sulphonic acids or mixtures of these.

When a lower molecular weight sulphonic acid is present, it is preferably an alkaryl sulphonic acid and most preferably a mixture of $C_9$ to $C_{30}$ and higher alkyl substituted alkyl benzene or alkyl toluene or alkyl xylene sulphonic acid. The alkyl group may be branched or straight chain. It is preferred that the lower molecular weight sulphonic acid has a number average molecular weight of at least 300, preferably at least 350. When low molecular weight sulphonic acids are employed, it is preferred that their use is kept to a minimum to avoid skin sensitisation which is believed to originate from the low molecular weight sulphonate derived from these acids.

The preferred high molecular weight sulphonic acids and when present lower molecular weight sulphonic acids are those which are derived from aromatic alkylates prepared from $C_2$, $C_3$ or $C_4$ polyolefins such as polyethylene, polypropylene or polynormal butene. It is most preferred that they are prepared from polynormal butene. It is also possible to prepare straight chain lower molecular weight sulphonic acids from aromatic alkylates prepared from straight chain hydrocarbons such as linear α-olefins.

When the sulphonic acid is a mixed sulphonic acid and is derived from polynormal butene, it is preferred that it has a number average molecular weight of at least 600 and preferably 600 to 700.

The diluent may be any suitable inert non-volatile oleaginous material or mixture of materials such as a mineral or synthetic oil, petroleum oil or it may be a solvent which is miscible with lubricating and fuel oils. If desired the high molecular weight sulphonic acid or mixture of sulphonic acids may be used in diluted form as a solution or dispersion in a diluent such as mineral or synthetic oil, petroleum oil, or any suitable inert oleaginous material or solvent.

The high base number sulphonates used in the method of this invention may be derived from low or high molecular weight sulphonic acids as hereinbefore defined and whose method of manufacture is discussed above. Their function in the present method is to supply some or all of the base needed in the process for the neutralisation of high molecular weight sulphonic acid or partially neutralised soap, to supply a portion of neutralised sulphonic acid for the final low base number sulphonate product and, importantly, to supply base to react with the added carboxylic acid to produce the required metal carboxylate to provide the required base number for the low base number sulphonate. The high base number sulphonate may be the source of some or all of any low molecular weight sulphonic acid which is present in the low base number sulphonates of the present invention. It is preferred that the high base number sulphonate is derived from the same high molecular weight sulphonic acid as used to prepare the low base number sulphonate of the present invention. It is preferred that the high base number sulphonate has a TBN of 100 or greater and most preferably 200 or greater.

The primary source of base for preparation of the high base number sulphonate or for the preparation of the partially neutralised soap as used in the method of the present invention or for the direct neutralisation of sulphonic acid in the method of the present invention is a Ca or Group 1 oxide or hydroxide and most preferably is a calcium hydroxide or oxide.

The excess base which is present from the high base number sulphonate reacts with the carboxylic acid present producing a carboxylate. Most of the excess base is converted to carboxylate. However, any excess base which does not react will remain as basic carbonate from the high base number sulphonate. As the excess base in the process is derived from the high base number sulphonate and is in the form of carbonate, there is little or no free hydroxyl present in the final product.

The carboxylic acid is essential to produce low viscosity products. However, the selection of suitable carboxylic acids is crucial. Not all carboxylic acids are suitable. Suitable carboxylic acids for this process are those in which the Ca or Group 1 metal salts of the acid are at least sparingly water-soluble. These acids may be mono, di-, tri-, or poly-carboxylic acids. They may be aliphatic or aromatic or contain heteroatoms such as for example sulphur although carboxylic acids which contain heteroatoms other than oxygen are not preferred. The suitable carboxylic acids may be saturated or unsaturated, ie contain a carbon to carbon double bond. Suitable monocarboxylic acids include linear or branched monocarboxylic acids such as for example formic acid, acetic acid, and propionic acid. Preferred monocarboxylic acids are $C_1$ to $C_8$ monocarboxylic acids. Suitable dicarboxylic acids include linear or branched $C_2$ to $C_8$ dicarboxylic acids such as for example oxalic acid, maleic acid, fumaric acid, adipic acid and succinic acid. Suitable tricarboxylic acids include for example citric acid. An example of a suitable sulphur containing acid is thioglycolic acid. Suitable aromatic acids include benzoic acid, phthallic acid and salicylic acid. A corresponding anhydride or half ester may be used in place of the dicarboxylic acid, e.g. succinic anhydride, phthallic anhydride or maleic anhydride. The preferred acids are dicarboxylic acids or their anhydrides; the most preferred dicarboxylic acid is succinic acid or its anhydride.

In the process of the present invention the carboxylic acid or anhydride reacts to produce a metal carboxylate which may be colloidally dispersed within the sulphonate soap in the product. In the process of the present invention, sufficient high base number sulphonate and carboxylic acid are used to generate enough metal carboxylate to provide a total base number for the composition of between 0–50 mg KOH $g^{-1}$, most preferably between 0–30 mg KOH $g^{-1}$.

The carboxylic acid, overbased high base number sulphonate and high molecular weight sulphonic acid or soap may be added to the reaction in any order. The high base number sulphonate can be added prior to the carboxylic acid or conversely the carboxylic acid can be added prior to the high base number sulphonate.

In one embodiment of the method of the present invention a low base number sulphonate can be prepared directly from the neutralisation of the desired high molecular weight sulphonic acid using a high base number sulphonate. In another embodiment the low base number sulphonate may be prepared from a partially neutralised soap which has been prepared from the reaction of a high molecular weight sulphonic acid and hydrated lime, CaO or $CaCO_3$ or similar. This partially neutralised soap is then reacted with a high base number sulphonate without having first been stripped of any solvent and water which may be present. Alternatively the partially neutralised soap is stripped of solvent and water before neutralisation with high base number sulphonate. The extent of neutralisation of the partially neutralised soap is that which is required to accommodate sufficient of the base from the high base number sulphonate in order to result in the final product having a low base number. The exact extent of neutralisation will depend on the base number of the high base number sulphonate and the concentration of reactants. It is preferred that at least 50% of the sulphonic acid groups present in the soap have been neutralised, more preferably at least 90% or greater or 95% or greater. It is preferred that the partial neutralisation of the high molecular weight sulphonic acid be taken to the maximum achievable neutralisation whilst keeping the viscosity of the soap at an acceptable value with a low level of sediment. Acceptable viscosity in relation to soaps is 300 cS or less and more preferably 200 cS or less. As neutralisation is continued to higher levels and approaches completion, the viscosity increases to a point, which may be reached at complete neutralisation, where the soap is a solid or semi-solid. It is preferred that the soap is as concentrated as possible and preferably comprises at least 50% by weight of a mixture of sulphonate and unreacted sulphonic acid. A key feature of the method of the present invention is that a high base number sulphonate is used to provide all or some of the base required for neutralisation of the high molecular weight sulphonic acid and to acid to produce a metal carboxylate. It is the use of a high base number sulphonate coupled with the use of a carboxylic acid which results in the low base number sulphonates of the present invention having low viscosities and no skinning.

If in the process of the present invention a high molecular weight sulphonic acid is used as a starting material for neutralisation it is preferred that the sulphonic acid is added to a polar solvent diluent mixture in which is dispersed the Ca or Group 1 metal oxide, hydroxide, carbonate or similar necessary for partial neutralisation of the acid to produce the partially neutralised soap in situ. Water is the preferred polar solvent but alcohols such as methanol, ethanol etc. and mixtures of water and alcohol are also suitable. It is preferred that the polar solvent/diluent mixture comprises between 1 and 50% by weight of water, methanol, ethanol or mixtures thereof and more preferably 15 to 35% by weight. The diluent is preferably a substantially neutral mineral oil synthetic oil or petroleum oil.

The polar material reduces the viscosity of the initial polar solvent/diluent mixture and is believed to aid dispersion of Ca or Group 1 metal oxide or hydroxide or carbonate or similar and also aid promotion of the neutralisation reaction. It is preferred that the polar solvent/diluent mixture is mixed with a solvent or mixture of solvents prior to the addition of the Ca or Group 1 metal oxide or high molecular weight sulphonic acid. Suitable solvents include aliphatic and aromatic solvents and mixtures thereof such as for example heptane, toluene and xylene. Preferred solvents are toluene and mixtures thereof with other solvents. These solvents aid the viscosity reduction and control during the reaction, aid the solubility of high molecular weight sulphonic acids and assist in the removal of water on completion of reaction by forming azeotropes during the stripping stages.

During the process exothermic reactions may occur: the reaction mixture temperature may be allowed to rise, or may be reduced or maintained by cooling. It is preferred that, during the neutralisation reaction, the temperature is maintained below 100° C., most preferably below 80° C., so that little or no water is lost from the mixture.

During the process a period of heat soaking may be beneficial after the addition of all the sulphonic acid, to allow the neutralisation to be completed before any further additions or process stages. During a heat soaking period it may be beneficial to maintain the temperature of the reaction mixture at a pre-determined level. It is preferred that the reaction temperature is increased, e.g. to 70° C. It is preferred that the heat soaking is for a period of at least 30 minutes and most preferably 1 hour.

On completion of the reaction substantially all of the water present in the reaction mixture and also any additional solvent which is present may be removed by stripping. The stripping may be carried out with nitrogen, with increased temperature of the reaction mixture, with gradual application of a vacuum or with a combination of all three.

During the process sediment may be formed which may be removed via filtration. It is preferred that sediment formation is as low as possible so that the amount of filtration required is kept to a minimum and is as fast as possible. During filtration a filter aid may be used, preferably a fine porosity filter aid e.g. diatomaceous earth. Filtration may be carried out at an elevated temperature e.g. at between 150°–160° C. and under applied pressure, e.g. 8 bar. A feature of the process of the present invention is that low levels of sediment are produced at completion of the reaction. This allows for the use of a simple polish filtration which reduces the need for filter aids and the subsequent problems associated with waste disposal. The process of the present invention typically produces sediment levels in the product of 0.6 vol % or less e.g. 0.5 vol % or less and preferably 0.2 vol % or less and most preferably 0.1 vol % or less without filtration.

If desired further additions of diluent may be made in order to obtain a desired final product viscosity, content of basic sulphonate or total base number. Preferably these additions are made after filtration. Additives such as antifoam agents may be added during the process or after filtration.

The process of the present invention produces low base number sulphonates which have low viscosity and good fluidity. They have low levels of chlorine because chlorine containing fluidisers as used in prior art processes are not required. They are low in hydroxyl content and do not exhibit skinning on exposure to the atmosphere. These products have also been determined not to be skin sensitisers when tested by Repeat Insult Patch Testing.

The low base number sulphonates of the present invention are useful as additives for oil-based compositions, for example, lubricants, and greases. The invention thus also provides such compositions containing the low base number sulphonates.

The amount of low base number sulphonate that should be used in the oil based composition depends on the type of composition and its proposed application. Automotive crankcase lubricating oils preferably contain 0.01% to 5 mass % of the low base number sulphonate, on an active ingredient basis, based on the mass of the oil.

The low base number sulphonates of the present invention are oil-soluble or (in common with certain of the other additives referred to below) are dissolvable in oil with the aid of a suitable solvent, or are stably dispersible materials. Oil-soluble, dissolvable, or stably dispersible as that terminology is used herein does not necessarily indicate that the materials are soluble, dissolvable, miscible, or capable of being suspended in oil in all proportions. It does mean, however, that the materials are, for instance, soluble or stably dispersible in oil to an extent sufficient to exert their intended effect in the environment in which the oil is employed. Moreover, the additional incorporation of other additives may also permit incorporation of higher levels of a particular additive, if desired.

Additives, including the low base number sulphonates of the present invention, can be incorporated into a base oil in any convenient way. Thus, they can be added directly to the oil by dispersing or by dissolving them in the oil at the desired level of concentration. Such blending can occur at room temperature or an elevated temperature.

Low base number sulphonates of the present invention are particularly useful in lubricating oil compositions which employ a base oil in which the mixtures are dissolved or dispersed. Base oils with which the low base number sulphonates may be used include those suitable for use as crankcase lubricating oils for spark-ignited and compression-ignited internal combustion engines, for example, automobile and truck engines, marine and railroad diesel engines. They may also be used, for example, in base oils suitable for use as aviation lubricants or as lubricants for two cycle engines. They may also be used in a base oil in a wide variety of other applications such as gear oils, automatic transmission fluids, tractor oils, metalworking fluids and anti-corrosion coatings. Suitable base oils may be natural or synthetic.

Synthetic base oils include alkyl esters of dicarboxylic acids, polyglycols and alcohols; poly-α-olefins, including polybutenes; alkyl benzenes; organic esters of phosophoric acids; and polysilicone oils.

Natural base oils include mineral lubricating oils which may vary widely as to their crude source, for example, as to whether they are paraffinic, naphthenic, mixed, or paraffinic-naphthenic, as well as to the method used in their production, for example, distillation range, straight run or cracked, hydrofined, solvent extracted and the like.

More specifically, natural lubricating oil base stocks which can be used may be straight mineral lubricating oil or distillates derived from paraffinic, naphthenic, asphaltic, or mixed base crude oils. Alternatively, if desired, various blended oils may be employed as well as residual oils, particularly those from which asphaltic constituents have been removed. The oils may be refined by any suitable method, for example, using acid, alkali, and/or clay or other agents such as, for example, aluminium chloride, or they may be extracted oils produced, for example, by solvent extraction with solvents, for example, phenol, sulphur dioxide, furfural, dichlorodiethyl ether, nitrobenzene, or crotonaldehyde.

The lubricating oil base stock conveniently has a viscosity of about 2.5 to about 12 cS (about $2.5 \times 10^{-6}$ to about $12 \times 10^{-6}$ $m^2/s$) and preferably about 2.5 to about 9 cS (about $2.5 \times 10^{-6}$ to about $9 \times 10^{-6}$ $m^2/s$) at 100° C. Mixtures of synthetic and natural base oils may be used if desired.

The low base number sulphonates of the present invention may be employed in a lubricating oil composition which comprises lubricating oil, typically in a major proportion, and the sulphonates, typically in a minor proportion, for example, in a proportion as indicated above. Additional additives may be incorporated in the composition to enable it to meet particular requirements. Examples of additives which may be included in lubricating oil compositions are other detergents and metal rust inhibitors, viscosity index improves, corrosion inhibitors, oxidation inhibitors, friction modifiers, dispersants, anti-foaming agents, anti-wear agents, pour point depressants, and rust inhibitors. Such additives are well known in the art.

As known in the art, some of these additives can provide a multiplicity of effects; thus for example, a single additive may act as a dispersant-oxidation inhibitor.

Compositions when containing the above-mentioned additives are typically blended into the base oil in amounts which are effective to provide their normal function. Representative effective amounts of such additives, if present, are illustrated as follows:

| Additive | Mass % a.i.* (Broad) | Mass % a.i.* (Preferred) |
|---|---|---|
| Detergents/Rust Inhibitors | 0.01–6 | 0.01–4 |
| Viscosity Modifier | 0.01–6 | 0.01–4 |
| Corrosion Inhibitor | 0.01–5 | 0.01–1.5 |
| Oxidation Inhibitor | 0.01–5 | 0.01–1.5 |
| Dispersant | 0.1–20 | 0.1–8 |
| Pour Point Depressant | 0.01–5 | 0.01–1.5 |
| Anti-foaming Agent | 0.001–3 | 0.001–0.15 |
| Anti-wear Agents | 0.01–6 | 0.01–4 |
| Friction Modifier | 0.01–5 | 0.01–1.5 |
| Mineral or Synthetic Base Oil | Balance | Balance |

*Mass % active ingredient based on the final oil

When a plurality of additives is employed, it may be desirable, although not essential, to prepare additive concentrates comprising the additives (the concentrate being referred to herein as an additive package) whereby several additives can be added simultaneously to the base oil to form the lubricating oil composition. Dissolution of the additive concentrate into the lubricating oil may be facilitated, for example, by mixing accompanied with heating, but this is not essential. The concentrate or additive package will typically be formulated to contain the additive(s) in amounts to provide the desired concentration in the final formulation when the additive package is combined with a predetermined amount of base lubricant. Thus, one or more low base number sulphonates prepared in accordance with the present invention can be added to small amounts of base oil or other compatible solvents along with other desirable additives to form additive packages containing active ingredients in an amount, based on the additive package, of, for example, from about 2.5 to about 90 mass %, and preferably from about 5 to about 75 mass %, and most preferably from about 8 to about 50 mass % by weight, additives in the appropriate proportions with the remainder being base oil.

The final formulations may employ typically about 10 mass % of the additive-package, the remainder being base oil.

The present invention further provides a lubricating oil composition which comprises a major amount of a lubricating oil and a minor amount of a calcium or Group 1 metal low base number sulphonate composition according to the present invention. Such a lubricating oil composition may be a low phosphorus composition, ie have a phosphorus content of 0.1 wt % or less, preferably 0.08 wt % or less and most preferably 0.05 wt % or less.

The present invention also provides a lubricating oil concentrate which comprises a calcium or Group 1 metal low base number sulphonate composition according to the present invention and one or more other lubricant additives.

The low base number sulphonate compositions of the present invention have been found to provide improved wear performance, particularly preferred being those which contain one of formate, fumarate, succinate, maleate, citrate or adipate, most preferably fumarate, maleate, succinate or citrate. Particularly preferred are the calcium low base number sulphonates, it being most preferred that the composition has a TBN of less than 24, preferably in the range of 5 to 24.

The invention is further illustrated by way of example only with reference to the following Examples.

Preparation of Neutral Calcium Sulphonate. Comparative Example A

Toluene (480 g), methanol (360 g), water (50 g) and a mineral oil diluent (175 g) were charged to a 2 litre glass reactor fitted with stirrer, reflux condenser, nitrogen purge, pressure compensated dropping funnel and temperature control. To this mixture, at ambient temperature, there was added calcium hydroxide (23.3 g). The calcium hydroxide had a purity, as measured by EDTA titration, of greater than 95%. The reaction mixture was then heated to 40° C. and a sulphonic acid solution (814 g) was then added, via the pressure compensated dropping funnel, over a 15 minute period whilst maintaining the temperature at 40° C. The sulphonic acid was a $C_{15}$–$C_{60+}$ mixture of alkyl benzene sulphonic acids with an number average molecular weight of 670 diluted to mass 60% with mineral oil.

On completion of the sulphonic acid addition the temperature of the reaction mixture was in creased to 60° C. and held at this temperature for 1 hour. Silicone antifoamant (100 ppm based on the total reactor charge) was then added and the apparatus then changed from a reflux to distillation configuration. The reactor contents were then heated from 60° C. to 68° C. over a 20 minute period, from 68° C. to 75° C. over 30 minutes and from 75° C. to 160° C. over 1 hour. During the distillation period a nitrogen purge of 100 cc/min. was employed. When the temperature had reached 160° C. a vacuum of 200 mm Hg absolute was applied and the vacuum treatment continued for 30 minutes.

A 50 ml sample was then removed from the reactor and dissolved in 50 ml of toluene. This mixture was then added to a 100 ml calibrated centrifuge tube. The solution was then centrifuged for 20 minutes at 1500 rpm and the volume of sediment in the tube measured. There was 0.25 $cm^3$ of sediment in the tube which equates to 0.5 vol % sediment in the reactor contents. The product, after a slow filtration, was a neutral calcium sulphonate with an active ingredient of 43.5 mass %. The kinematic viscosity of the product at 100° C. was 663 cS which is unacceptably high.

100 ml of the product was poured into a 250 ml beaker. The beaker was stored at ambient and periodically checked, by inclining it at an angle, to see if a skin had formed on the surface. The product skinned.

Preparation of a Low Base Number Calcium Sulphonate from a High Molecular Weight Sulphonic Acid Using a Conventional Process. Comparative Example B A mineral diluent oil (259 g) and water (110.3 g) were mixed in a 2 liter reactor fitted with stirrer, reflux condenser, nitrogen purge, pressure compensated dropping funnel, cooling coil and temperature control. Calcium hydroxide (41.3 g) of purity, by EDTA titration of greater than 95%, was then added and the temperature adjusted to 30° C. Formic acid (17.9 g) was then added via the dropping funnel. An exothermic reaction occurred. Cooling was applied to maintain the temperature at 37° C. A 60% by mass solution of a $C_{15}$–$C_{60+}$ alkyl benzene sulphonic acid (314.2 g) in mineral oil was then added to the reactor and the temperature of the resultant exothermic reaction controlled with further cooling so that the temperature did not exceed 70° C. The number average molecular weight of the sulphonic acid employed was 670. Following the sulphonic acid addition the temperature was held at 70° C. for 1 hour after which time a second charge of calcium hydroxide (17.7 g) was added. A further charge of sulphonic acid (314.2 g) was then added and the resultant exotherm controlled by cooling so that the reaction temperature did not exceed 80° C. After the second acid addition the temperature was stabilised at 80° C. for 1 hour. The apparatus was then changed from a reflux to a distillation mode and heat was applied. The temperature of the reaction mixture was increased from 80° C. to 110° C. over 4 hours and then from 110° C. to 160° C. over a 2 hour period. A vacuum of 400 mbar absolute was then applied for one hour whilst maintaining the temperature at 160° C. to remove the volatile components.

A 50 ml sample of the product was removed from the reactor and the amount of sediment determined by the method described in Comparative Example A. There was 2.6 vol % sediment in the reactor. The product was viscous with a kinematic viscosity at 100° C. of 1670 centistokes. An attempt to filter the product was unsuccessful due to the high level of sediment combined with the high viscosity.

This example illustrates that the preparation of a low base number calcium sulphonate from a high molecular weight sulphonic acid using a conventional low base number process suitable for low molecular weight sulphonic acids leads to an unacceptable sub standard product.

Preparation of a High Base Number Calcium Sulphonate (For Use in Example 1 Below)

A High Base Number Calcium Sulphonate from a $C_{16}$–$C_{60+}$ mixed alkyl benzene sulphonic acid of number average molecular weight of 670 was prepared by a conventional overbasing process. This involved the neutralisation of the sulphonic acid with an excess of calcium hydroxide in a mixed toluene/polar solvent system. The excess of calcium hydroxide was then converted to colloidal calcium salts by carbonating the mixture. The volatile solvents were then removed by distillation. The final product was a high base number calcium sulphonate of total base number (TBN) 295 mg KOH/g, with a calcium sulphonate content of 29 mass % and a kinematic viscosity at 100° C. of 110 centistokes.

Example 1—Preparation of a Low Base Number Calcium Sulphonate Directly From Sulphonic Acid Toluene (303 g), water (50.5 g) and a mineral diluent oil (259.9 g) were charged to a 2 liter glass reaction vessel equipped with stirrer, reflux condenser, nitrogen purge, pressure compensated dropping funnel and temperature control. To this mixture there was added 21.4 g of calcium hydroxide of 98.8% purity, as measured by EDTA titration. The temperature of the mixture was adjusted to 50° C. and 686 g of a 60% by mass solution of a $C_{16}$–$C_{60+}$ mixed alkyl benzene sulphonic acid of average number molecular weight of 670, in mineral oil, added to the reactor via the dropping funnel over a 15 minute period. On completion of the addition the temperature of the reaction mixture was adjusted to 70° C. and held at this temperature for 1 hour after which time 100 ppm of silicone antifoamant (based on the total reactor charge) was added. To this reaction mixture 48.9 g of the high base number sulphonate, described above, was added over a 5 minute period. A formic acid solution (80%) 10.2 g was then added whilst maintaining the temperature at 70° C. Following the formic acid addition the temperature was held at 70° C. for a further 15 minutes to ensure complete reaction. The apparatus was then changed from a reflux to distillation configuration and the volatile solvents removed by distillation to 160° C. over 1 hour. A vacuum of 200 mm Hg. absolute was then applied for 30 minutes to remove the last traces of solvent. The sediment level was then determined by the method described in Comparative Example A. There was 0.06 vol. % sediment in the reactor contents. The product was then filtered using 0.5 mass % of diatomaceous filter aid. The filtration was extremely rapid giving a finished product as a clear brown mobile liquid with a kinematic viscosity at 100° C. of 45.5 centistokes, a total base number of 10.2 mg KOH/g, a calcium sulphonate content of 43.7 mass %, a calcium content of 1.6 mass % and a chlorine content of 5 ppm.

100 ml of the filtered material was poured into a 250 ml beaker and then left to stand at ambient temperature. There was no tendency for the product to skin when exposed to the air.

Calculation of the total hydroxide content based on the method and product charges, show a potential for 0.11 mass % calcium hydroxide in the finished product. This is lower than the calculated level for products made by the conventional process where 0.7% mass % is the calculated value.

Examples 2 and 3—Preparation of Low Base Number Calcium Sulphonates Directly From Sulphonic Acid The general method of Example 1 was repeated except the charge quantities of reactants given in Table 1 were employed. The products were low in viscosity, the sediment prior to filtration was low and the filtered product did not skin when exposed to air.

TABLE 1

| Reactor Charges (grams) | Example 1 | Example 2 |
|---|---|---|
| Toluene | 299.8 | 233.6 |
| Water | 50.2 | 49.8 |
| Diluent Oil | 249.8 | 297.0 |
| Calcium Hydroxide (98.8% purity) | 23.6 | 23.4 |
| $C_{16}$–$C_{60+}$ Alkyl Benzene Sulphonic Acid Solution | 678.6 | 672.2 |
| High Base Number Sulphonate | 62.4 | 76.0 |
| Formic Acid | 14.4 | 18.5 |
| Product Properties | | |
| Kinematic viscosity at 100° C., cS | 44 | 45.5 |
| Sediment prior to Filtration, vol % | 0.06 | 0.08 |
| Total Base Number, mg kOH/g | 14.3 | 18.0 |
| Calcium Sulphonate Content, mass % | 43.7 | 43.5 |
| Chlorine Content, ppm | 5 | 5 |
| Calcium Content, mass % | 1.79 | 1.92 |

Both examples have low viscosity and low chlorine contents. A conventional low base number sulphonate synthesised with a halide fluidiser would contain 0.5 mass % chlorine.

SOAP 1—Preparation of a Partially Neutralised Sulphonic Acid (90% Neutralised)

Toluene (480 g), methanol (360 g), water (50 g) and Diluent Oil (175 g) were charged into a 2 liter glass reactor equipped with stirrer, reflux condenser, nitrogen purge, pressure compensated dropping funnel and temperature control. Calcium Calcium hydroxide of 98.8% purity (25.5 g) was added and the temperature adjusted to 40° C. A $C_{16}$–$C_{60+}$ alkyl benzene sulphonic acid solution (814 g) was added via the dropping funnel over a 15 minute period. The number average molecular weight of the sulphonic acid was 670 and the solution contained 60 mass % sulphonic acid in diluent oil. On completion of the addition the temperature was adjusted to 60° C. and then held at this temperature for 1 hour. The apparatus was then changed from a reflux to distillation configuration and 100 ppm of silicone antifoamant (based on the reactor contents) added. The reaction mixture was then heated to 160° C. and a vacuum of 210 mm Hg. absolute applied to remove the volatile components. The final product was a solution of calcium sulphonate and sulphonic acid in diluent oil and had a kinematic viscosity at 100° C. of 137 centistokes. The ratio of sulphonic acid which had been neutralised and converted to the calcium salt to that retained in the product as unreacted sulphonic acid being 9:1.

SOAP 2—Preparation of a Partially Neutralised Sulphonic Acid (95% Neutralised)

The procedure as described for SOAP 1 was repeated with the exception that 26.9 g of calcium hydroxide was used.

This produced a product which was 95% neutralised as calcium sulphonate with the remaining 5% of the sulphonic acid remaining unreacted. The final product had a kinematic viscosity at 100° C. of 250 centistokes.

EXAMPLE 4—Preparation of a Low Base Number Calcium Sulphonate From Partially Neutralised Sulphonic Acid SOAP 1 (100 g), as prepared above, was added to a 250 ml reaction vessel equipped with condenser, stirrer, nitrogen purge and temperature control. The partially neutralised acid was heated to 60° C. and the High Base Number Sulphonate described above (5.8 g) was added. After the addition Formic Acid of 80% purity (1.2 g) was added. The temperature of the reactor contents was then held at 60° C. for 20 minutes before changing the apparatus from a reflux to distillation mode. The temperature was then increased to 160° C. over 45 minutes before applying a vacuum for a further 20 minutes. The product had a sediment level of 0.1 vol. %, a TBN of 24 mg KOH/g, a calcium sulphonate content of 43.9 mass %, a calcium content of 2.18 mass % and a Kv 100° C. of 58 centistokes.

When tested in the exposure to air test, as described in Comparative Example A, the product did not skin.

EXAMPLE 5—Preparation of Low Base Number Calcium Sulphonate From Partially Neutralised Sulphonic Acid SOAP 2 (100 g), as prepared above, was added to a 250 ml reaction vessel equipped as that described above. The method of EXAMPLE 4 was repeated with the exceptions that the amount of High Base Number Sulphonate employed was 9.1 g and the amount of Formic acid used was 2.55 g. The finished product had a sediment level of 0.05 vol %, a TBN of 24 mg KOH/g, a calcium sulphonate content of 42.6 mass %, a calcium content of 2.08 mass % and a Kv 100° C. of 55 centistokes. This product did not skin when exposed to air.

Comparative Example C—Preparation of Low Base Number Calcium Sulphonate from a Low Molecular Weight Sulphonic Acid The process of EXAMPLE 1 was repeated with the exception that the high molecular weight sulphonic acid was replaced with a mixed low molecular weight sulphonic acid made up of $C_{24}$ average alkyl benzene sulphonic acid and a $C_{12}$ average alkyl xylene sulphonic acid with a number average molecular weight for the mixture of 440. The resultant sulphonate was an extremely viscous, non flowing product at ambient temperature with a TBN of 12 mg KOH/g which skinned when exposed to air.

This example illustrates that sulphonic acids consisting of entirely of low molecular weight species are not suitable for producing low base number calcium sulphonates which have low viscosity and are non skinning when exposed to air.

EXAMPLES 6 to 18

The general method of EXAMPLE 1 was repeated with a number of different carboxylic acids and anhydrides being used in place of the formic acid. The results along with details of variations to the general method are presented in Table 2.

All of these low base number sulphonates were low in chlorine and did not skin on exposure to air.

In Examples 15,16 and 17 the carboxylic acid was added to the reaction prior to the high base number sulphonate.

Comparative Example D. Preparation of a Low Base Number Calcium Sulphonate using a Halide Promoter 611 g of a mixed low molecular weight sulphonic acid made up of a C24 average alkyl benzene sulphonic acid and a C12 average alkyl xylene sulphonic acid with a number average molecular weight of 440 and 249.9 grams of a mineral diluent oil were charged to a 2 liter glass reactor fitted with a stirrer, reflux condenser, nitrogen sparge and temperature control. The mixture was heated to 60° C. when 15.7 g of a 35 mass % solution of calcium chloride in water, 11.8 g of formic acid and 12.9 g of water were added. There was an exothermic reaction and the temperature increased to 65° C. The temperature was set to 65° C. and 54.1 g of calcium hydroxide added. Again an exothermic reaction occurred which increased the temperature to 80° C. when a further 72.9 g of water was added. The temperature was adjusted to 85° C. and held at this temperature for 1 hour. The apparatus was then changed from a reflux to distillation mode and the temperature increased from 85° C. to 110° C. over 4 hours. At 110° C. a nitrogen sparge of 200 $cm^3$/minute was applied and the temperature increased to 160° C. over 2 hours. A vacuum of 400 mbar. absolute was then applied for 30 minutes. A 50 $cm^3$ sample was then removed from the reactor and the sediment level determined by dissolving in toluene and centrifuging under the conditions in Comparative Example A. There was 0.5 vol % sediment in the product which was then filtered using a diatomaceous filter aid to give a low base number calcium sulphonate with the following properties: –TBN 23 mg KOH/g, calcium sulphonate content of 43.5 mass %, calcium content of 2.9 mass % and a kinematic viscosity at 100° C. of 40 centistokes. The chlorine content was 0.35 mass %. The product skinned when exposed to air.

This example illustrates that low viscosity low base number calcium sulphonates can be prepared from low molecular weight sulphonic acids but halides are required to control the viscosity.

TABLE 2

| EXAMPLE NO. | 6 | 7 | 8 | 9 | 10 | 11 | 12 |
|---|---|---|---|---|---|---|---|
| Carboxylic Acid Anhydride | Succinic Acid | Maleic Anhydride | Fumaric Acid | Adipic Acid | Octanoic Acid | Citric Acid | Benzoic acid |
| Amount of Carboxylic Acid Anhydride, g | 10..1 | 8.5 | 10.1 | 12.6 | 25 | 11.8 | 20.9 |
| Toluene, g | 303 | 303 | 303 | 303 | 303 | 303 | 303 |
| Water, g | 54 | 54 | 54 | 54 | 54 | 54 | 54 |
| Diluent Oil g, | 242 | 242 | 242 | 242 | 242 | 242 | 242 |
| Sulphonic Acid 60% Solution in Oil, g | 686 | 686 | 686 | 686 | 686 | 686 | 686 |
| High Base Number Sulphonate, TBN 297 mg KOH/g | 54 | 54 | 54 | 54 | 54 | 54 | 54 |
| Calcium Hydroxide, g | 20.7 | 20.7 | 20.7 | 20.7 | 20.7 | 20.7 | 20.7 |
| Calcium Sulphonate, mass | 43.5 | 43.5 | 43.5 | 43.5 | 43.5 | 43.5 | 43.5 |
| Total Base Number, mg KOH/g | 12.9 | 12.8 | 13.1 | 13.0 | 12.7 | 10.8 | 12.1 |
| Sediment, vol % | 0.06 | 0.2 | 0.2 | 0.04 | 0.04 | 0.06 | 0.06 |
| Kinematic Viscosity at 100° C., centistokes | 41 | 40 | 190 | 50 | 9400 | 56 | 640 |

Wear Performance

Various low base number sulphonates were evaluated for their wear performance using a SMIRA Valve Train Wear Rig; this apparatus is described in test method CEC L-31-T-81. The version used in this evaluation was a monocam rig. which describes a Cam and Follower Test Machine. The following three temperature test protocols were used:

TABLE 3

| Oil Temperature °C | Cam Speed RPM | Time Mins | Load Kg |
|---|---|---|---|
| 40 | 250 | 30 | 20 |
|  |  | +60 | 60 |
| 65 | 1500 | 30 | 20 |
|  |  | +60 | 60 |
| 120 | 1500 | 30 | 20 |
|  |  | +60 | 60 |

Two lubricating oil formulations were evaluated.

Formulation 1 was prepared in mineral basestock using a conventional viscosity modifier, a dispersant, a proprietary detergent package, a mixture of antioxidants including a ZDDP. Formulation 2 was prepared in a mixed mineral and synthetic basestock using the same additives as Formulation 1 but with the addition of an aromatic amine antioxidant and an additional ZDDP thus providing a formulation with a mixture of ZDDP's. In each Formulation the Ca low base number sulphonate was evaluated at a concentration of 0.9 wt % based on the weight of the formulation.

Oil performance was evaluated in terms of tappet wear in microns at the end of the test. The results for Formulation 1 are shown in Table 4 and the results for formulation 2 are shown in Table 5. A negative value for Delta indicates an improved wear performance relative to the low base number sulphonate derived from low molecular weight sulphonic acid.

TABLE 4

|  |  | 65 Degrees | | 120 Degrees | |
|---|---|---|---|---|---|
| Test Number | Calcium Low Base Number Variant | Cam Wear (microns) | Delta | Cam Wear (microns) | Delta |
| 1 | Calcium Low Base Number Sulphonate from low Molecular Weight Sulphonic Acid | 5.80 |  | 6.80 |  |
| 2 | Formic Acid 8 TBN | 5.71 | −0.09 | 6.43 | −0.37 |
| 3 | Succinic Acid 12 TBN | 6.40 | 0.60 | 6.10 | −0.70 |
| 4 | Fumaric acid 12 TBN | 4.71 | −1.09 | 5.43 | −1.37 |
| 5 | Adipic Acid 12 TBN | 5.40 | −0.40 | 9.30 | 2.5 |
| 6 | Maleic Acid 12 TBN | 4.70 | −1.10 | 8.7 | 1.9 |
| 7 | Citric Acid 12 TBN | 6.40 | 0.6 | 7.6 | 0.8 |

TABLE 5

|  |  | 45 degrees | | 65 Degrees | | 120 Degrees | |
|---|---|---|---|---|---|---|---|
| Test Number | Calcium Low Base Number Variant | Cam Wear (microns) | Delta | Cam Wear (microns) | Delta | Cam Wear (microns) | Delta |
| 8 | Calcium Low Base Number Sulphonate from low Molecular Weight Sulphonic Acid | 4.30 |  | 6.60 |  | 7.30 |  |
| 9 | Formic Acid 12 TBN | 4.79 | 0.49 | 7.43 | 0.83 | 5.36 | −1.94 |
| 10 | Succinic Acid 12 TBN | 3.00 | −1.30 | 4.90 | −1.70 | 6.70 | −0.60 |
| 11 | Fumaric Acid 12 TBN | 3.00 | −1.30 | 4.86 | −1.74 | 7.43 | 0.13 |
| 12 | Adipic Acid 12 TBN | 3.90 | −0.40 | 3.00 | −3.60 | 9.40 | 2.10 |
| 13 | Maleic Acid 12 TBN | 2.10 | −2.20 | 5.00 | −1.60 | 7.10 | −0.20 |
| 14 | Citric Acid 12 TBN | 3.30 | −1.00 | 3.90 | −2.70 | 6.00 | −1.30 |

We claim:

1. A calcium or Group 1 metal low base number sulphonate composition comprising from at least 10% by weight of at least one sulphonate prepared from neutralisation of a sulphonic acid having a number average molecular weight of 500 or greater, being an oil-soluble synthetic sulphonic acid or an alkaryl sulphonic acid; a calcium or Group 1 metal carboxylate; and diluent, wherein the sulphonate composition has 0.5% by weight or less of hydroxide expressed as the calcium or group 1 metal hydroxide, and has a chloride content of 100 ppm by weight or less.

2. The composition of claim 1 wherein at least 20% by weight of said at least one sulphonic acid is present.

3. The composition of claim 2 wherein at least 40% by weight of said at least one sulphonate is present.

4. The composition of claim 1 having 0.25% by weight of the hydroxide or less.

5. The composition of claim 1 having a chloride content of 50 ppm by weight or less.

6. The composition of claim 1 wherein the sulphonic acid has a number average molecular weight of 600 or greater.

7. The composition of claim 1 wherein the sulphonic acid is a $C_{15}$ to $C_{60+}$ alkyl-substituted alkaryl sulphonic acid.

8. The composition of claim 1 wherein the sulphonic acid has alkyl substitution derived from poly(normal butene) polymers.

9. The composition of claim 1 having 0.6 vol % or less of sediment.

10. A calcium or Group 1 metal low base number sulphonate composition comprising from at least 10% by weight of at least one sulphonate prepared from neutralisation of a sulphonic acid having a number average molecular weight of 500 or greater, being an oil-soluble synthetic sulphonic acid or an alkaryl sulphonic acid; a calcium or group 1 metal carboxylate; and diluent wherein the composition has 0.6 vol % or less of sediment.

11. A method for the preparation of a calcium or Group 1 metal low base number sulphonate composition which comprises neutralising a sulphonic acid, or partially neutralised soap thereof, and a carboxylic acid, with a high base number sulphonate, the sulphonic acid having a number average molecular weight of 500 or greater, being an oil-soluble synthetic sulphonic acid or an alkaryl sulphonic acid.

12. The method of claim 11 wherein the soap is prepared in situ by partially neutralising a sulphonic acid with an oxide or hydroxide of calcium or of a Group 1 metal.

13. The method of claim 11 or 12 wherein the high base number metal sulphonate is derived from a sulphonic acid as defined in claim 11.

14. A calcium or Group 1 metal low base number sulphonate composition obtainable by the method of claim 11.

15. A lubricating oil composition comprising a major amount of a lubricating oil and a minor amount of a composition of claim 1.

16. The composition of claim 15 having a phosphorus content of 0.1 wt % or less.

17. A lubricating oil concentrate comprising a composition of claim 1, and one or more other lubricant additives.

18. A lubricating oil composition comprising a major amount of a lubricating oil and a minor amount of a composition of claim 10.

19. A lubricating oil composition comprising a major amount of a lubricating oil and a minor amount of a composition made by the process of claim 11.

20. A lubricating oil concentrate comprising a composition of claim 10, and one or more other lubricant additives.

21. A lubricating oil concentrate comprising a composition made by the process of claim 11, and one or more other lubricant additives.

* * * * *